(12) United States Patent
Hong

(10) Patent No.: US 6,478,739 B1
(45) Date of Patent: Nov. 12, 2002

(54) ULTRASONIC BREAST EXAMINATION SYSTEM

(75) Inventor: Hyundae Hong, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/854,024

(22) Filed: May 11, 2001

(51) Int. Cl.[7] ................................................. A61B 8/00
(52) U.S. Cl. ........................ 600/437; 128/915; 128/916
(58) Field of Search ................................. 128/915, 916, 128/660; 600/437; 73/618

(56) References Cited

U.S. PATENT DOCUMENTS

| | | |
|---|---|---|
| 3,964,296 A | 6/1976 | Matzuk |
| 4,075,883 A | 2/1978 | Glover |
| 4,083,232 A | 4/1978 | Heyser et al. |
| 4,121,468 A | 10/1978 | Glover et al. |
| 4,174,634 A | 11/1979 | Dory |
| 4,206,763 A | 6/1980 | Pedersen |
| 4,246,791 A | 1/1981 | Glenn |
| 4,282,880 A | 8/1981 | Gardineer et al. |
| 4,298,009 A | 11/1981 | Mezrich et al. |
| 4,338,948 A | 7/1982 | Perez-Mendez et al. |
| 4,339,952 A | 7/1982 | Foster |
| 4,341,222 A | 7/1982 | Gardineer et al. |
| 4,347,850 A | 9/1982 | Kelly-Fry et al. |
| 4,362,058 A | 12/1982 | Abele |
| 4,433,690 A * | 2/1984 | Green et al. ............... 128/915 |
| 4,509,368 A | 4/1985 | Whiting et al. |
| 4,545,385 A | 10/1985 | Pirschel |
| 4,594,895 A | 6/1986 | Fujii |
| 4,681,120 A | 7/1987 | Kunii |
| 4,747,411 A | 5/1988 | Ledley |
| 4,821,728 A | 4/1989 | Ledley |
| 4,852,577 A | 8/1989 | Smith et al. |
| 5,079,698 A | 1/1992 | Grenier et al. |
| 5,280,788 A | 1/1994 | Janes et al. |
| RE34,566 E | 3/1994 | Ledley |
| 5,333,612 A | 8/1994 | Wild |
| 5,546,945 A | 8/1996 | Soldner |
| 5,603,326 A | 2/1997 | Richter |
| 5,673,697 A | 10/1997 | Bryan et al. |
| 5,709,206 A | 1/1998 | Teboul |
| 5,776,062 A | 7/1998 | Niekls |
| 5,979,457 A | 11/1999 | Rohrberg |
| 6,039,694 A | 3/2000 | Larson et al. |
| 6,213,840 B1 | 4/2001 | Han |

FOREIGN PATENT DOCUMENTS

| | | |
|---|---|---|
| WO | WO 94/14375 A1 | 7/1994 |
| WO | WO 00/55616 A1 | 9/2000 |

\* cited by examiner

*Primary Examiner*—Marvin M. Lateef
*Assistant Examiner*—Ruby Jain
(74) *Attorney, Agent, or Firm*—David M. Weirich; Jay A. Krebs; Jeffrey R. Moore

(57) ABSTRACT

A wearable breast tissue examination device including a support element adapted to fit over at least a portion of a breast of the wearer. The support element has a shell, a measurement apparatus including at least two mutually opposed ultrasound transducer arrays disposed on at least a portion of the inner surface of the shell and at least one bladder element disposed in the shell that is configured to orient the wearer's breast properly for examination. The wearable device may also include means for operatively connecting the two mutually opposed transducer arrays to a transducer driver, and means for holding the support element on the wearer during use.

30 Claims, 13 Drawing Sheets

ULTRASONIC BREAST EXAMINATION SYSTEM

FIELD OF THE INVENTION

The present invention relates to a system for examination of breast tissue, preferably self-examination of breast tissue by transmitting ultrasonic radiation through the tissue to be examined. The examination system of the present invention can be portable and/or wearable and has the advantage of being readily adaptable for home use as well as being highly accurate.

BACKGROUND OF THE INVENTION

Breast cancer is a disease that affects many women and men throughout the world. The death rate for women with breast cancer in the United States is estimated to exceed one in nine women and the death rate for un-diagnosed cases is even higher. The high mortality rates are due to the ease in which this disease can metastasize through blood vessels and lymph nodes. As with many types of cancer, it has been found that accurate and early diagnosis is important to reducing the rate of mortality among those affected. In most cases, breast self-examination and routine mammography are the principal means for detecting breast abnormalities at early stage of malignant development. However, the cost, discomfort and availability of mammography and the lack of knowledge about how to perform a proper self-examination reduce the chances that an individual will be diagnosed with breast cancer early enough to significantly increase the chances that the individual will be able to survive the disease. Through many clinical studies, it is also shown that breast cancer can be curable if it is found at its early stage when the treatment can be effective.

Thus, there is a long felt need for a simple procedure for breast tissue examination which is non-invasive, and which can be conducted accurately and in the privacy of a medical office or in the home. To this same end, there is a need for a tissue examination system which is capable of accurately detecting irregularities in tissue density so as to aid medical personnel in ascertaining whether certain tissues are cancerous, pre-cancerous, or otherwise benign.

SUMMARY OF THE INVENTION

The present invention meets the aforementioned need in that it has been surprisingly discovered that human breast tissue can be non-invasively examined to accurately determine the presence of irregularities in tissue density. This non-invasive examination can be conducted using a device that provides an ultrasonic signature of the breast tissue by transmitting ultrasonic waves from an ultrasonic transmitting transducer through the breast to an ultrasonic receiving transducer. In one embodiment, at least a portion of the device is wearable and includes a support element adapted to fit over at least a portion of a breast of the wearer. The support element includes a shell having an opening, a perimeter defined by the opening, an inner surface that faces the breast of the wearer during use and an outer surface opposed to the inner surface. The support element further includes a measurement apparatus having at least two mutually opposed ultrasound transducer arrays, the transducer arrays being disposed on at least a portion of the inner surface of the shell. Preferably, the support element also includes at least one bladder element disposed adjacent at least a portion of one of the mutually opposed ultrasound transducer arrays and/or the inner surface of the shell, the bladder configured so as to orient the wearer's breast for examination. The wearable breast examination device also includes means for operatively connecting the two mutually opposed transducer arrays to a transducer driver, and means for holding the support element on the wearer during use.

DETAILED DESCRIPTION OF THE INVENTION

The present invention relates to a device, preferably a wearable device, for determining the presence of irregular tissue density. The present invention also relates to a device capable of providing an accurate location of the irregular tissue density within the area being examined. In one preferred embodiment, the device is adapted to examine the breast tissue of a user. The device can be adapted to examine one or both of the breasts at one time. Further, the device can be used by a patient at a location remote from a hospital or a physician's office, such as at home or a place of business. The information obtained by the device can be stored, printed or relayed to any suitable location for diagnosis.

Figure 1:
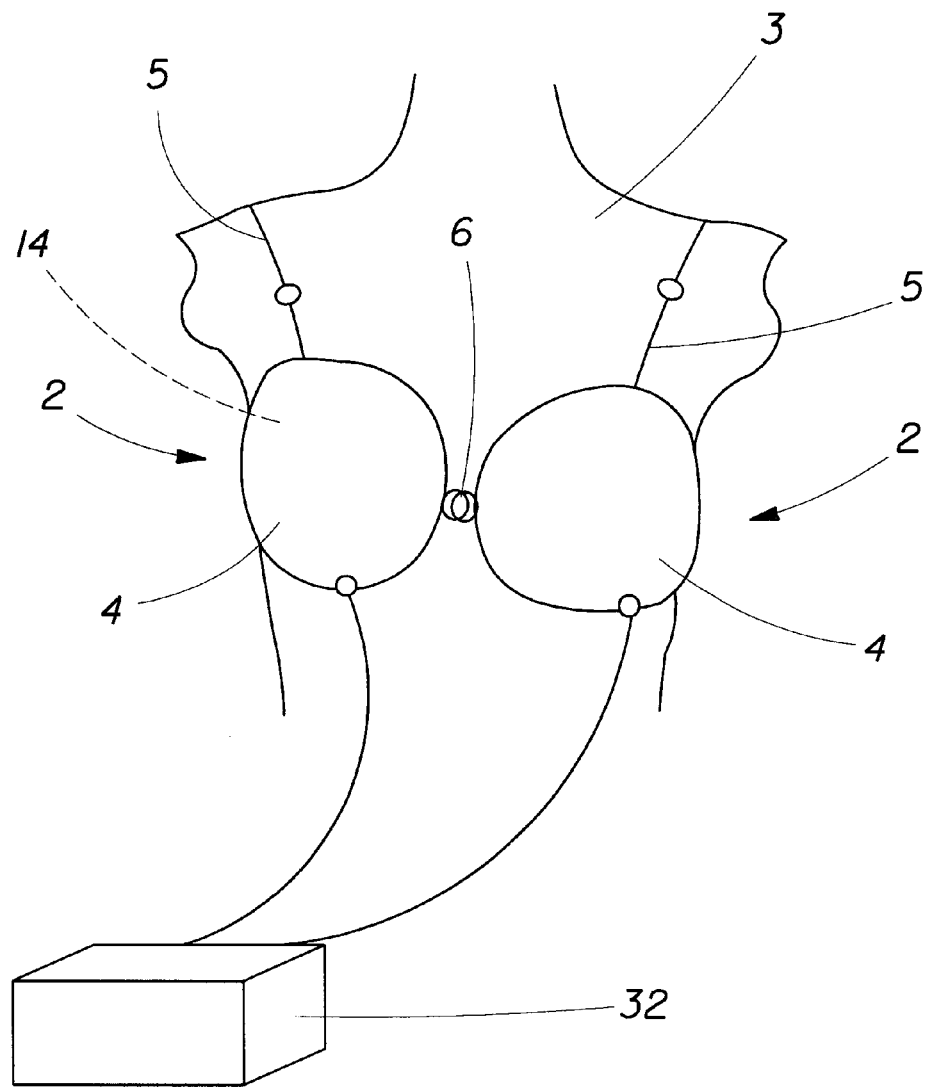
FIG. 1 is a front view of one embodiment of the breast tissue-examining device of the present invention shown on a user.
Figure 2:
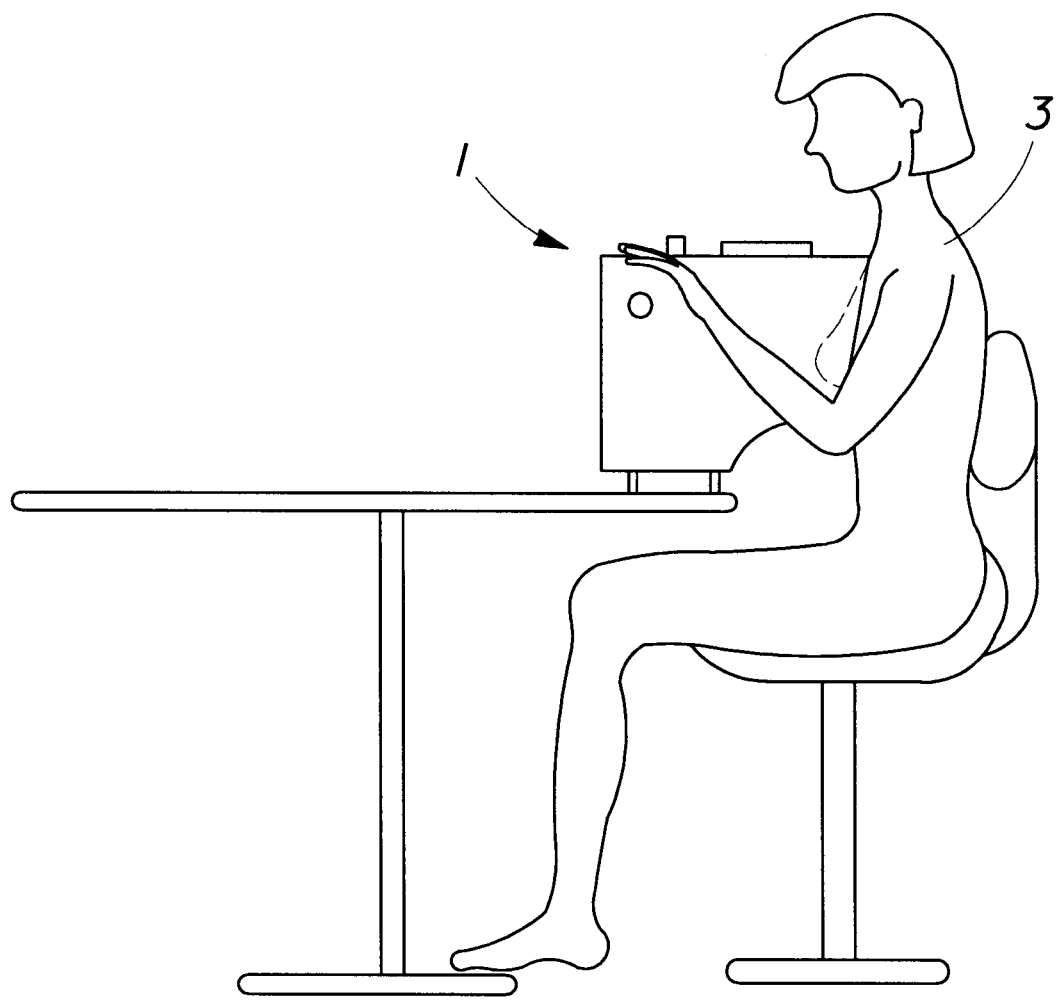
FIG. 2 is the alternative embodiment of the device of the present invention.

In one preferred embodiment of the present invention, the device is at least partially wearable by the user. As used herein, the term "wearable" refers to devices that are adapted to be worn by the user throughout at least a period of time during the examination of the tissue. That is, the size, configuration and makeup of the device are such that at least a portion of the device can be placed on the user and held in place thereon for some period of time during use. An example of a wearable embodiment of the present invention is shown in FIG. 1. In contrast, non-wearable devices are not placed on the wearer, but rather that are freestanding or supported on a table or other structure. Such non-wearable devices typically require that the user be placed into the device or positioned next to the device during use. An example of a non-wearable embodiment of the present invention is shown in FIG. 2.

Figure 3:
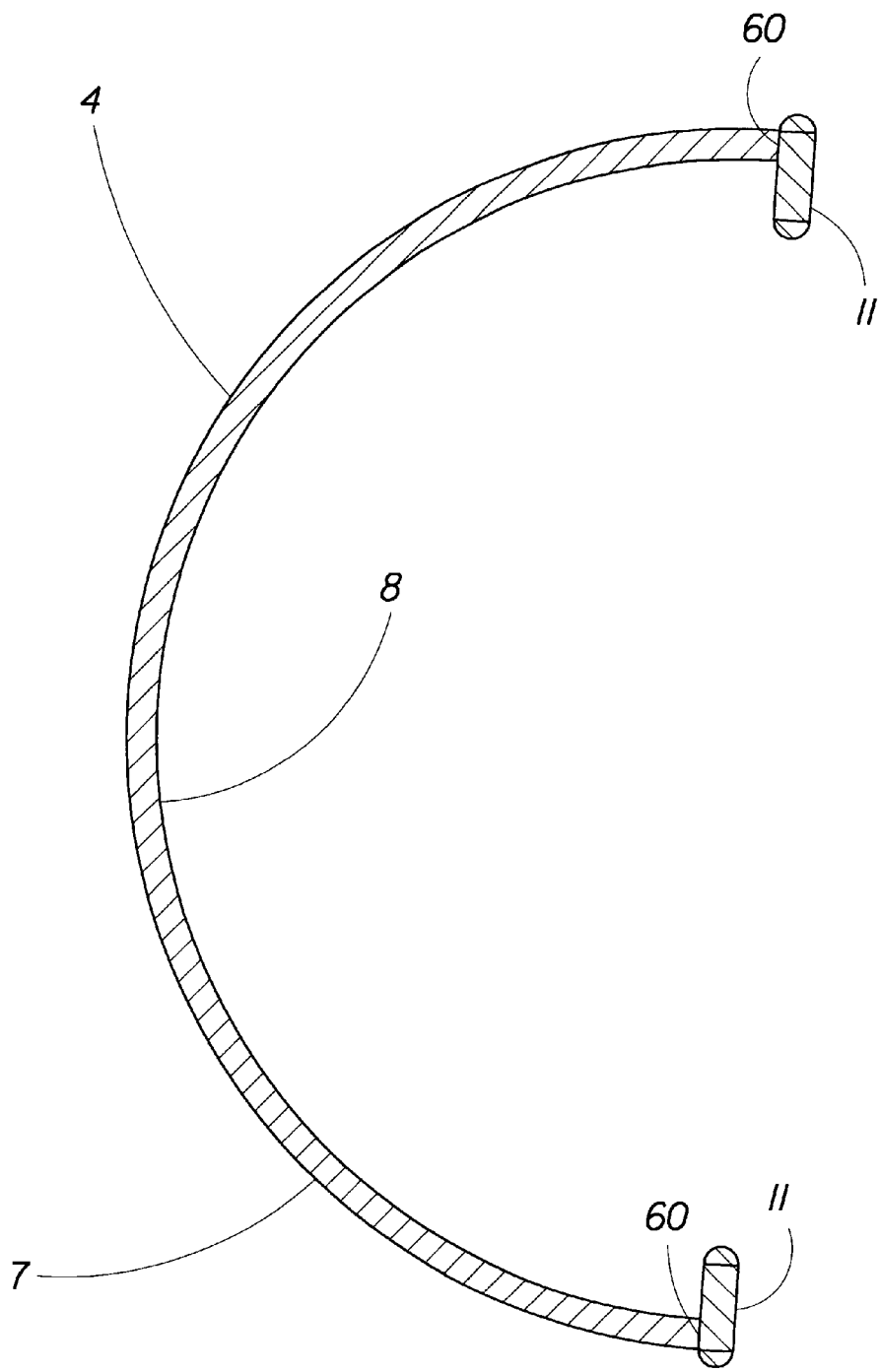
FIG. 3 is an enlarged, cross sectional view of the shell portion of the present invention.

As noted above, FIG. 1 shows one example of a wearable embodiment of the present invention. The breast examination device 1 includes at least one support element 2 adapted to fit over the breast 14 of the wearer 3. The support element 2 acts to hold the breast 14 in a proper position for examination as well as holding other components of the device 1. The support element 2 may be of any suitable size and shape and be made from any material suitable for use in connection with the examination of the wearer's breast 14. In one embodiment, the support element 2 may comprise a semi-rigid or rigid generally hemispherical shell 4. As can be seen in FIGS. 1 and 3, in a preferred embodiment, the shell 4 may be shaped similarly to the cup of a brassiere. Exemplary materials from which the shell 4 may be formed include plastics, foams (e.g., Styrofoam or other semi-rigid or rigid foams), rubbers, wood, ceramic, metals, silicones and the like.

The support element(s) 2 of the device 1 may include or be joined to one or more straps 5. The straps 5, as shown in FIG. 1, help maintain the support elements 2 in place about the wearer during use. The straps 5 may be made from any suitable material, but are preferably non-irritating to the wearer's skin. Exemplary straps 5 can be made from and configures similarly to the straps of a brassiere and may be adjustable to fit a range of wearers. Alternatively, the supporting elements 2 may be held in place by elastic bands, adhesive, a garment (e.g., a halter top), or any other known means or combinations thereof. Further, if the device 1 includes two support elements 2, the support elements 2 may be connected directly or indirectly to each other, such as for example, by a clasp 6.

FIG. 3 is a cross-sectional view of an exemplary generally hemispherical shell 4 having an outer surface 7 and an inner surface 8. The shell 4 preferably has a perimeter 60 defining the opening of the shell 4. In certain preferred embodiments, a cushion 11 is disposed adjacent at least a portion of the perimeter 60 of the shell 4, as shown in FIG. 3. The cushion 11 may act to help conform the support element 2 to the wearer and to hold it in place on the wearer during use. The cushion II may also be adapted to provide for an airtight seal against the wearer's body. The cushion 11 may comprise foam, a natural or synthetic rubber, an adhesive such as a hydrogel adhesive, or any other resilient material suitable for use against a human body.

Figure 4:
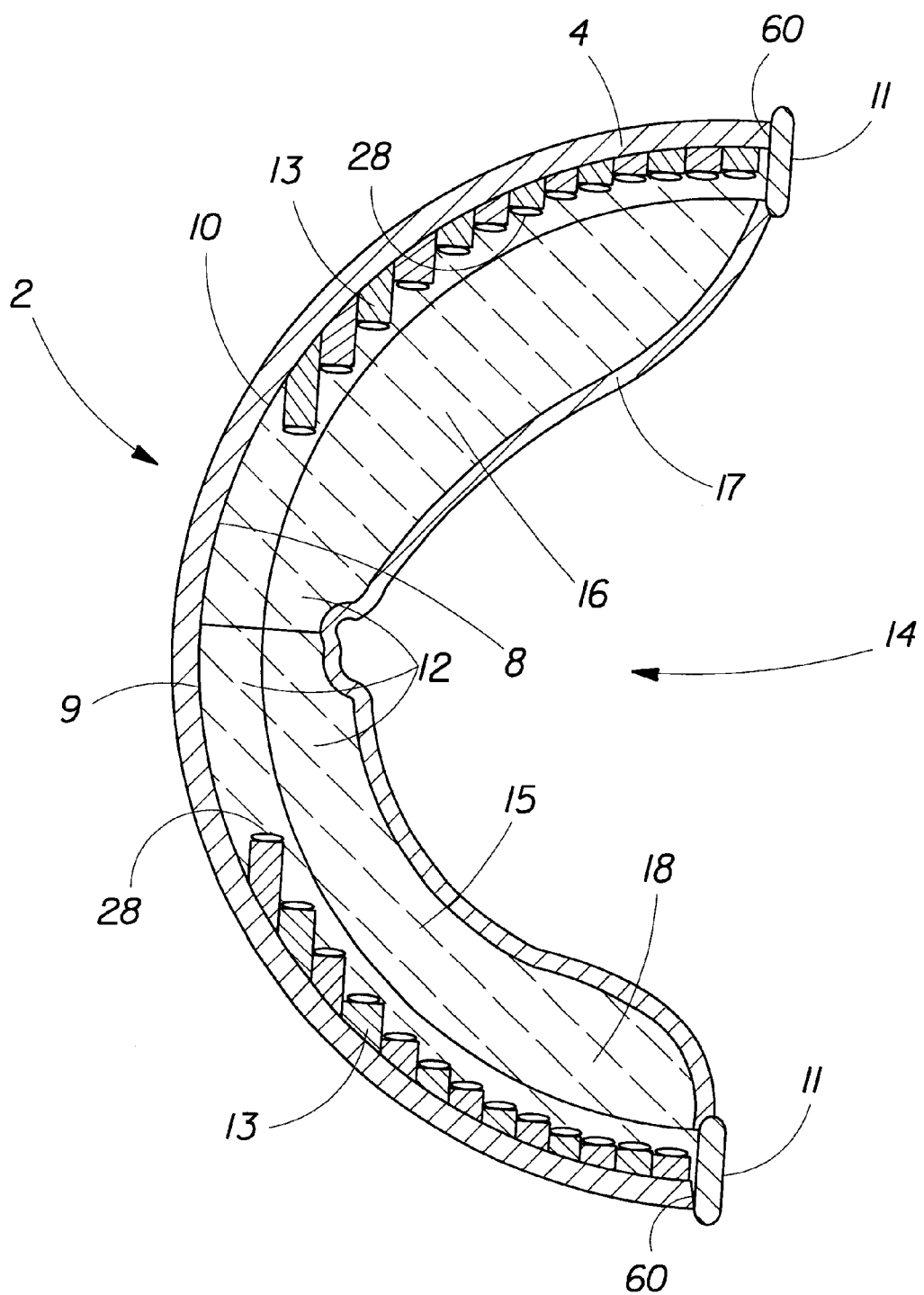
FIG. 4 is an enlarged cross-sectional view of the shell portion of the present invention shown with the flexible bladder expanded.
Figure 5:
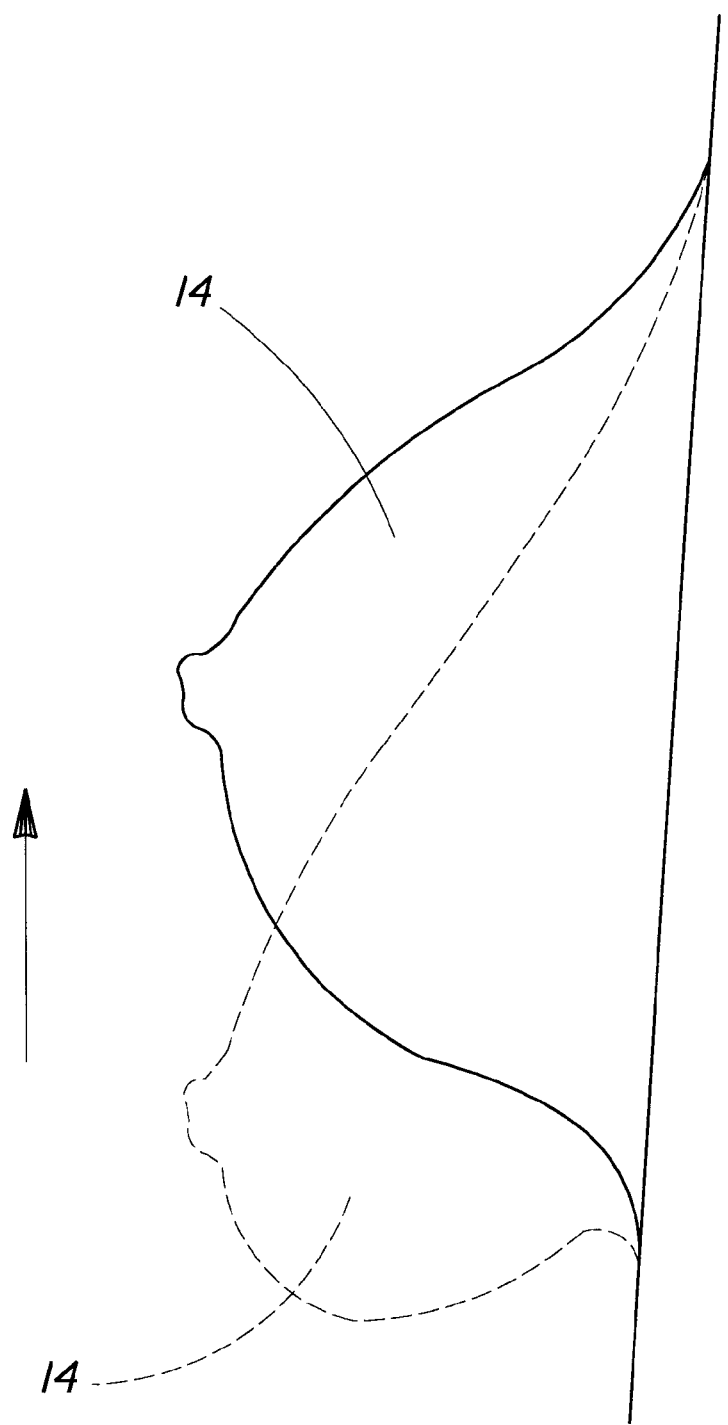
FIG. 5 depicts a human female breast in an unsupported position and in a supported position.

In preferred embodiments of the present invention, the support element 2 includes at least one bladder 12 (FIG. 4). The bladder structure 12 preferably creates a comfortable and complete coupling between a subject's breast 14 and the measurement apparatus 13 mounted on the inner surface 8 of the shell 4. Further, the bladder(s) 12 act to properly orient the breast 14 of the wearer 3 for the examination and to promote proper transmission between the measurement apparatus 13 and the breast tissue. Specifically, the bladder (s) 12 lift up the breast 14 and help ensure that the breast tissue is more uniformly distributed for scanning by measurement apparatus 13. (FIG. 5 shows an exemplary human female breast 14 in cross-section shown in a supported position (solid line) and an unsupported position (dotted line).) If the breast 14 is not first lifted into a supported position, wherein the breast tissues are not overlapping or constricted partially or overall, the outcome of the exam can be susceptible to non-uniform distribution of breast tissue mass. This can lead to a reduced ability to detect and locate the exact position of different density tissue regions that are indicative of abnormal tissue.

As shown in FIG. 4, the support element 2 preferably includes a first bladder 15 disposed adjacent at least a portion of the inner surface 8 of the shell 4 and a second bladder 16 disposed adjacent a different portion of the inner surface 8 of the shell 4. In the embodiment shown in FIG. 4, the first bladder 15 is disposed adjacent the lower inner surface 9 of the shell 4 and the second bladder 16 is disposed adjacent the upper inner surface 10 of the shell 4. (The terms "upper" and "lower" as used herein refer to relative locations determined when the examination device 1 is being used and the wearer 3 is seated or standing upright. Therefore, in this embodiment, the upper bladder 15 is generally located toward the cranial direction while the lower bladder 16 is generally located toward the caudate direction). The upper bladder 16 and lower bladder 15 are preferably expanding independently. The lower bladder 15 is preferably expanded first to lift up the breast 14 to a proper position and then the upper bladder 16 is expanded to gently compress the breast 14 for efficient coupling with the breast tissue. FIG. 4 depicts the upper and lower bladders 15, 16 in a filled, inflated state.

Of course, any number of bladders 12 can be used and the location of the bladders in the support element 2 can be varied. Further, each bladder 12 can include any number of internal cells or chambers that can be filled together or independently with the same or different materials. In any case, it is generally preferred that regardless of the arrangement, the bladders 12 be configured to expel substantially all of the air from around the breast 14 such that the bladder 12 is in intimate contact with the surface of breast 14. In certain embodiments, all or a portion of the bladder 12 may be covered with another material or part of the breast examination device 1 such that the bladder 12 itself is not in contact with the breast tissue, but rather the other material or part of the device 1 is in direct contact with the breast tissue once the air is expelled by the bladder(s) 12. In some circumstances, it may be desirable to apply a material, such as an acoustic coupling medium 17 between at least a portion of the bladder 12 and the breast skin to help maintain an airtight seal between the bladder 12 and the breast tissue. Preferably, the material that is applied between the bladder 12 and breast tissue to help maintain the seal is generally acoustically transparent so as not to distort or negatively affect the results of the examination.

In embodiments wherein the measurement apparatus 13 includes an ultrasonic transducer, the bladders 12 are preferably filled with an acoustic transmission medium 18. The acoustic transmission medium 18 preferably transmits ultrasonic waves with attenuation similar to normal human female breast tissue. The function of the acoustic transmission medium 18 is to deliver ultrasonic waves to the breast tissue being examined with minimum attenuation along the path through bladder 12 and acoustic coupling medium 17. The bladders 12 can be filled with any suitable acoustically conductive or transparent material. As used herein the terms "acoustically conductive" and "acoustically transparent" are used herein to mean any material that does not significantly alter the transmission or affect the reception of a particular predetermined ultrasonic signal. Non-limiting examples of suitable acoustic transmission media include water, silicones such as silicone oils, polyurethane, bio-grade saline and the like.

Figure 6:
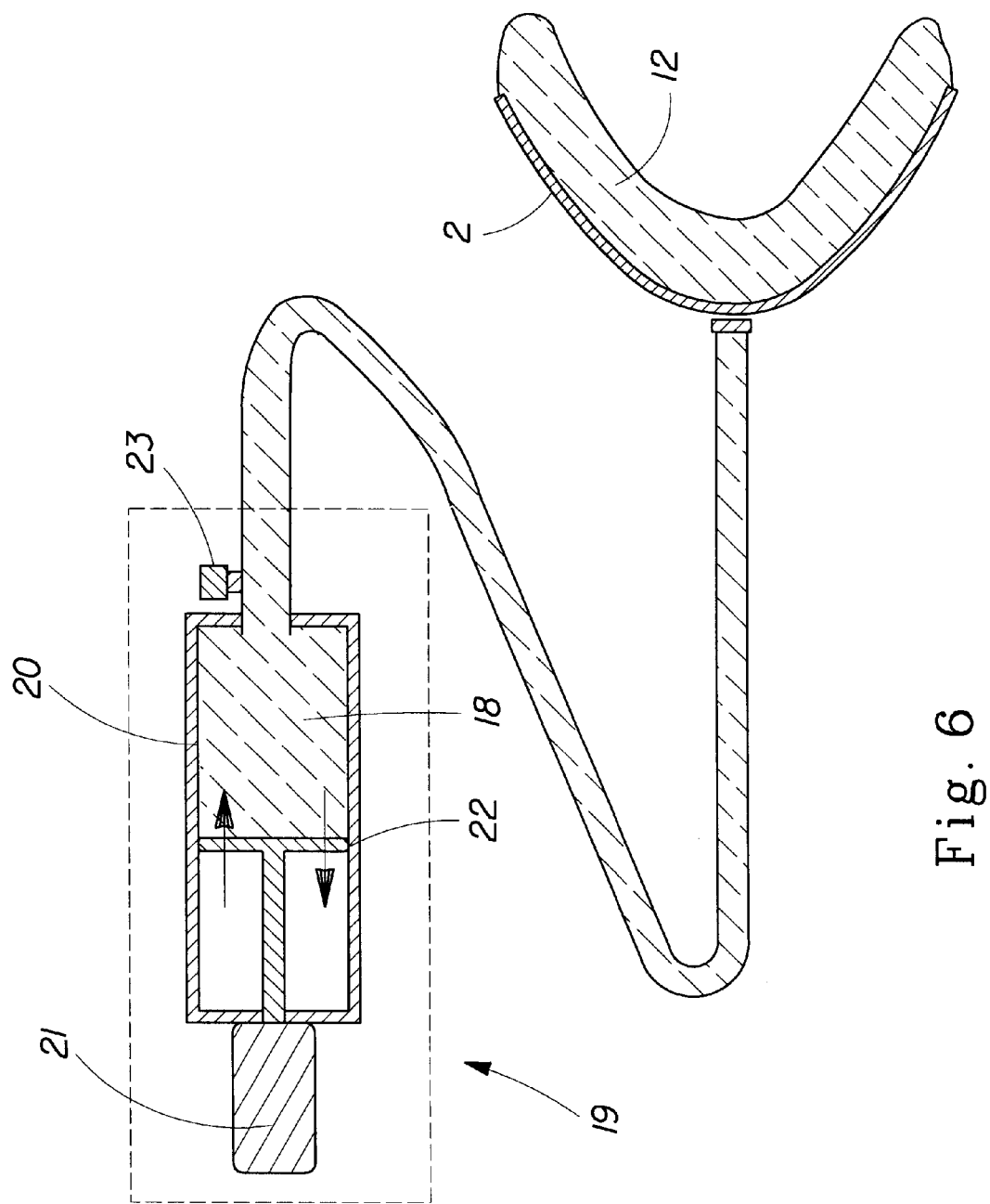
FIG. 6 is a cross-sectional view of a portion of the device of the present invention, including a reservoir and piston.

The bladder(s) 12 may be pre-filled or fillable upon use. If the bladders are not pre-filled, the bladders 12 may be filled via a bladder filling mechanism 19, one example of which is shown in FIG. 6. The bladder filling mechanism 19 may include a reservoir 20 including the acoustic transmission medium 18. The bladder filling mechanism 19 including the reservoir 18 may be a part of the wearable or non-wearable portion of the device 1 or may be a separate device, such as a handheld fluid containing bulb or syringe, to be used in conjunction with the examination device 1. The bladder filling mechanism 19 may include any mechanism known in the art to transport a liquid or semi-liquid material, including hand pumps, positive displacement pumps, rotary pumps, syringes, and the like. In one exemplary embodiment, as shown in FIG. 6, the bladder filling mechanism 19 includes an actuator 21 that moves a plunger 22 to change the volume of the acoustic transmission medium 18 in the bladder 12. When the actuator 21 pushes the plunger 22 to expand the bladder(s), the bladder 12 conforms to the breast 14 being examined (e.g. FIG. 4). One exemplary bladder filling mechanism 19 includes at least one electric motor and at least one driver integrated circuit, such as the Motorola MC33192 Stepping Motor Controller that controls the actuator 21 and moves the plunger(s) 22 to fill the bladders.

Regardless of the bladder filling mechanism 19 employed, the pressure level within the bladders 12 may affect breast comfort and the quality of the acoustic coupling between the breast 14 and the bladders 12 and/or other portions of the device 1. Therefore, in a preferred embodiment of the present invention, the bladder(s) 12 may be controlled so as to provide the desired benefits (e.g. support, minimizing acoustic attenuation, etc.) while providing reasonable comfort to the wearer. The wearer 3, the caregiver or any other persons involved in the examination, may manually control the bladder(s) 12. Alternatively, the bladders 12 may be controlled by a microprocessor or any electronic controller means or mechanism capable of affecting the expansion of the bladder(s) 12. In any case, the controller or controlling mechanism may affect the rate of expansion of the bladder(s) 12, the pressure exerted by the bladder(s) 12 on the breast 14 and/or the final configuration of the bladder(s).

The bladder filling mechanism 19 may include a pressure sensor 23 to help the user, wearer 3 and/or a microprocessor to monitor the pressure in the bladder 12. The information provided by the sensor 23 can be used to adjust the pressure in the bladder and/or the rate of filling or emptying of the bladder 12. In general, a pressure in the bladder 12 of between about 0.1 psi and about 5 psi is suitable for examination of human breast tissue. However, different pressure levels may be more suitable for different cup sizes, or different breast parenchyma (breast tissue mass). A filling rate generating pressure increases of between about 0.2 psi/sec and about 0.5 psi/sec are generally suitable to ensure reasonable comfort to the wearer, although other rates are possible.

As noted above, in certain preferred embodiments of the present invention, an acoustic coupling medium 17 may be applied to the interface between the bladder 12 and the breast skin. The acoustic coupling medium 17 facilitates the transmission of ultrasonic signals across the boundary between the breast skin and the bladder 12, ensuring that minimal attenuation of the signal occurs. The acoustic coupling medium 17 may be applied to the breast skin or the bladder surface and may comprise any known material capable of transmitting ultrasonic waves. Exemplary materials include water, hydrogels, silicones, polyurethanes, and the like. The acoustic coupling medium 17 may be applied in any form, but is preferably a liquid, semi-solid, gel, or paste form.

Figure 7:
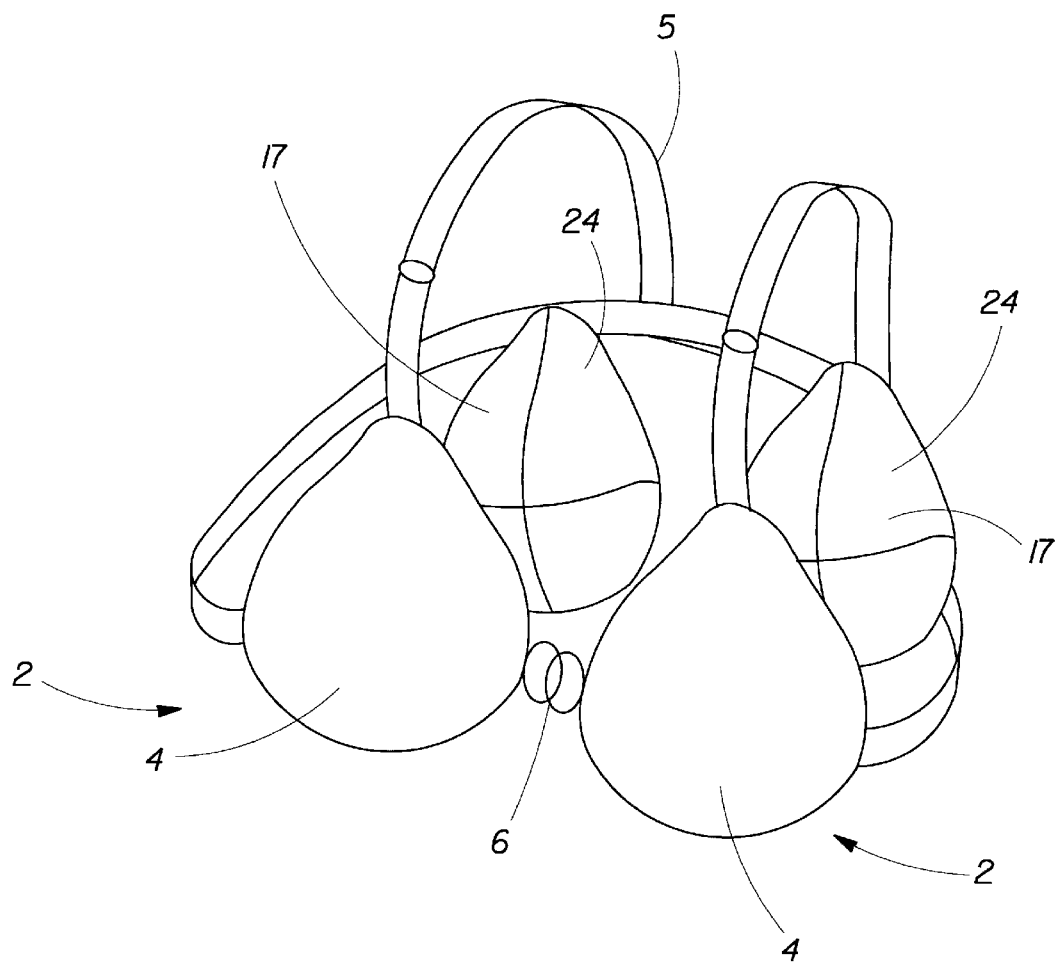
FIG. 7 is an isometric view of one embodiment of the present invention including straps and insert liners.

In certain preferred embodiments, as shown in FIG. 7, the acoustic coupling medium 17 may be disposed on an insert liner 24 that can be placed between the bladder and the breast. The insert liner 24 may be similar to a regular bra cup or breast pad and may be available for different cup sizes. The insert liner 24 may be made from or have disposed thereon the acoustic coupling medium 17. The insert liner 24 may be reusable or disposable and may comprise materials suitable for use with the device of the present invention. In one exemplary embodiment, the liner 24 may comprise a hydrogel or cellulose fiber which is wetted prior to examination, such as CMC fiber available from Acordis Specialty Fibers of Coventry, UK disposed on a support substrate such as a nonwoven, film, foam, tissue, etc. The liner 24 may additionally comprise an adhesive such as a pressure sensitive or water activatable adhesive to help keep the liner 24 in place during use.

Figure 8:
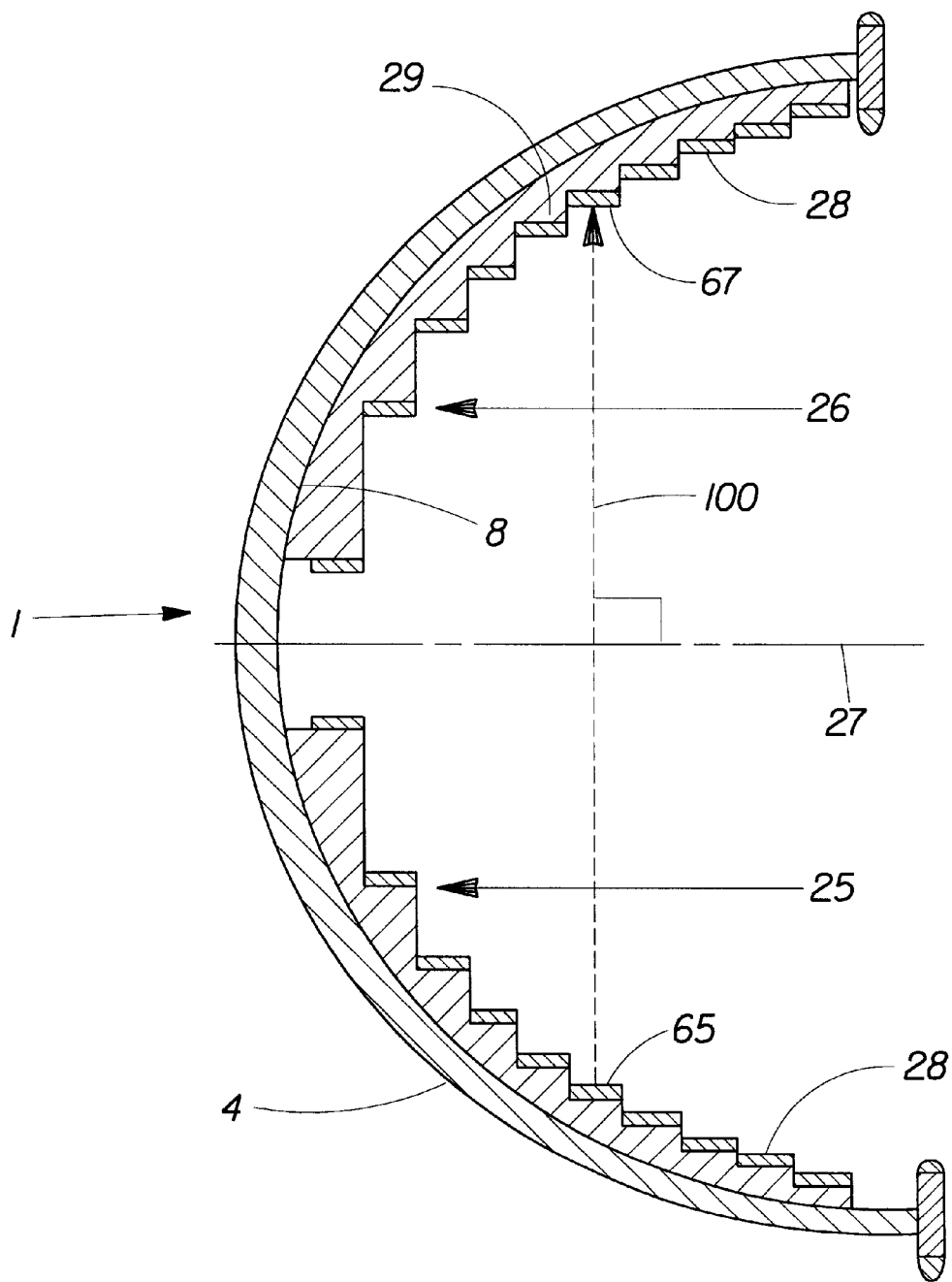
FIG. 8 is an enlarged, cross-sectional view of the shell portion of the present invention showing two mutually opposed ultrasound transducer arrays within the shell.
Figure 9A:
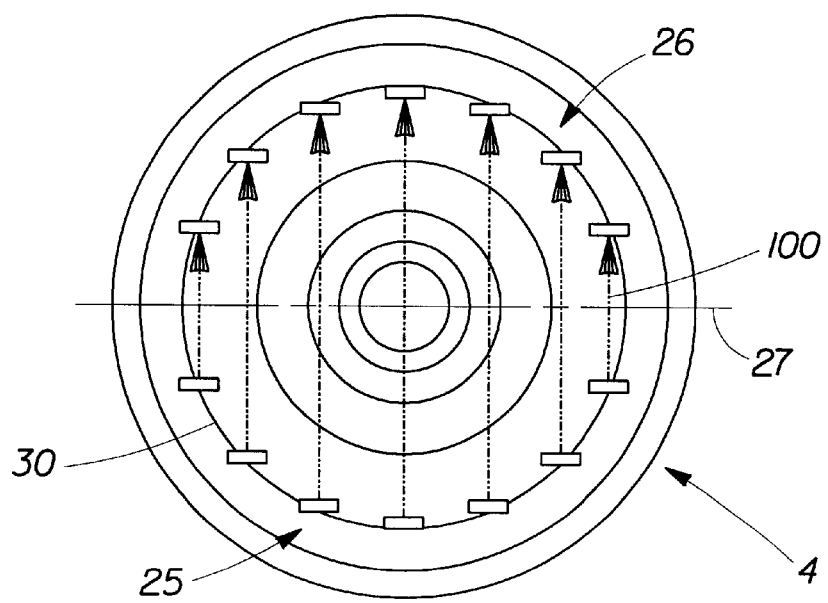
FIG. 9A shows a plan view of an exemplary terrace configuration for supporting the transducer arrays within the shell. The transducers are shown in a parallel array arrangement.

The breast examination device 1 of the present invention additionally comprises at least two mutually opposed ultrasound transducer arrays, such as the first transducer array 25 and second transducer array 26 shown in FIG. 8. By "mutually opposed" it is meant that the transducer arrays are aligned in a facing configuration such that an ultrasonic pulse from a transmitting transducer in the first transducer array 25 is received by a receiving transducer in the second transducer array 26 (or vice-versa) after the pulse has passed through the intervening breast tissue. Therefore, as shown in FIG. 8, in one preferred embodiment, the first transducer array 25 includes a transducer 28 having a first transducer face or transmitting surface 65 and the second transducer array 26 includes a transducer 28 having a second transducer face or receiving surface 67 which is opposed to the transmitting surface 65 and generally parallel thereto. The mutually opposed transducer pairs may also be configured in a parallel array pattern, as is shown in FIG. 9A. In such embodiments, the signal of the transmitting transducer (represented by line 100) intersects plane 27 that bisects the shell 4 at an angle of about 90 degrees. FIG. 9A shows an exemplary embodiment of the parallel array pattern, as it would appear in plan view looking into the shell 4 toward the inner surface 8. As can be seen, the ultrasonic waves (represented by the number 100) propagate in a direction generally perpendicular to the bisecting plane 27. This is due to the transducers being disposed along the annulus of the concentric rings 30 shown in FIG. 9A with the faces of the transducers parallel to the bisecting plane 27. The resulting image from data generated by transducers in this configuration can be similar to that of a cranial-caudate image from mammography.

Figure 9B:
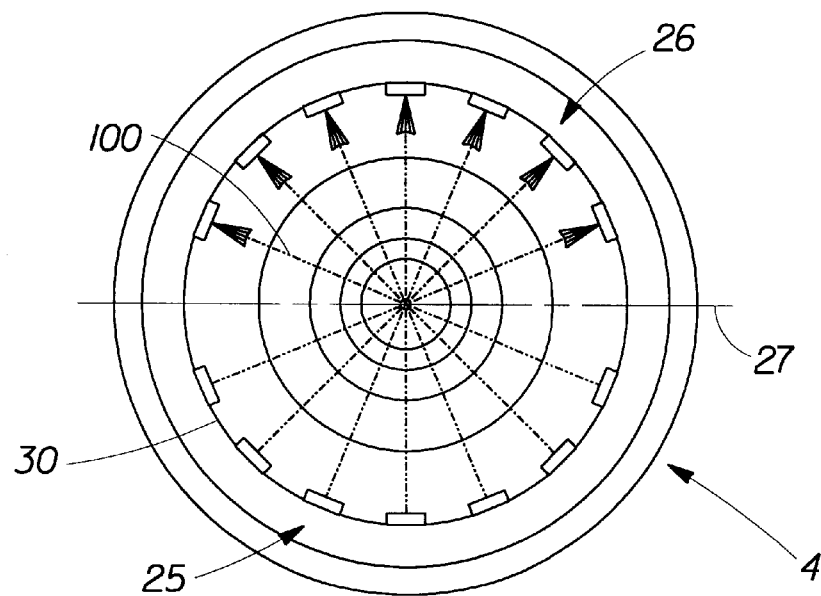
FIG. 9B shows a plan view of an exemplary terrace configuration for supporting the transducer arrays within the shell. The transducers are shown in a radially symmetrical array arrangement.
Figure 13:
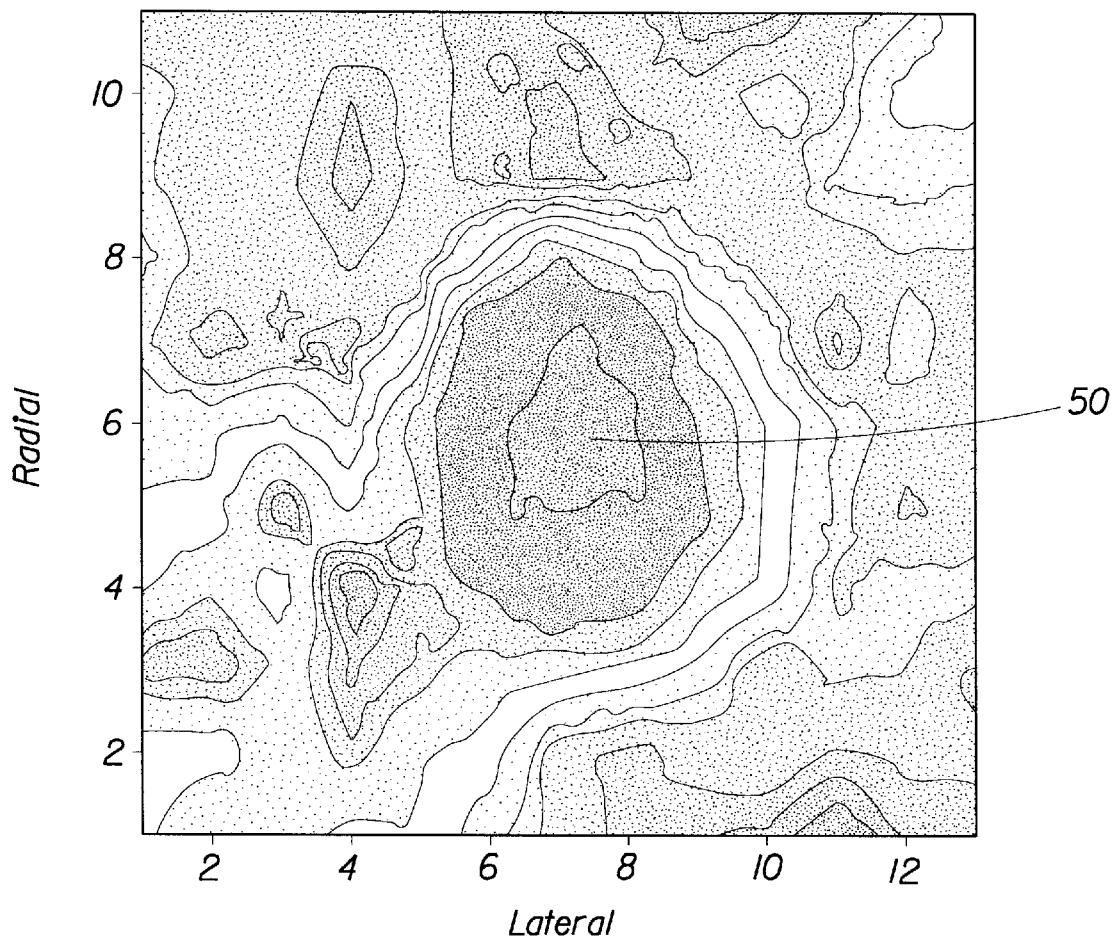
FIG. 13 shows an exemplary result of an exam representing the detection of an abnormality in a breast model.

In an alternative embodiment the transducers may be arranged in a radially symmetrical array pattern, as is shown in FIG. 9B. Preferably, the transducers in such a pattern are arranged to cover surround substantially the entire perimeter of the breast. In such embodiments, the transducers 28 are installed along the perimeter of at least one ring 30 in mutually opposed transmitter and receiver pairs. The mutually opposed pairs face each other, but are not necessarily oriented in any particular way with respect to the bisecting plane 27. Rather, the mutually opposed pairs are disposed within the shell so as to be located along the perimeter of annulus of the concentric ring(s) 30. Therefore, as shown in FIG. 9B, the ultrasonic waves 100 from each of the mutually opposed pairs of transducers are directed at different angles to the bisecting plane 27. However, each of the waves 100 passes generally through the centerpoint 110 of the shell 4. In such embodiments, the results can provide the user with tomographic images similar to those that are obtained from computerized tomography or magnetic resonance imaging. One example of an output that can be obtained from such a system is shown in FIG. 13.

Each transducer array may include one or more transducers. Preferably, each transducer array may comprise a multiplicity of transducers 28 which, as shown in the embodiment depicted in FIG. 8, may be mounted on terraces 29 formed on the inner surface 8 of the shell 4 so as to align the first and second transducer arrays in a mutually opposed configuration. In one embodiment, as shown in FIG. 9, the terraces 29 form concentric rings 30 extending throughout the inner surface 8 of the shell 4. However, embodiments are contemplated wherein the terraces 29 are disposed on only a portion of the inner surface 8 of the shell 4, and/or are somewhat irregularly arranged within the shell 4. The transducers 28 may be joined to the terraces 29 by any known means, including, for example, an epoxy glue such as Loctite® 330 adhesive-elastometric, Rocky Hill, Conn.

The number of rows of transducers 28 as well as the total number of transducers 28 may vary based on the size of the device 1 and/or the size of the subject's breasts. In any case, it is preferred that enough transducers 28 are used such that the entire area of examination (e.g. width and height of the breast) is surrounded by transducers. In one exemplary embodiment each transducer array may include several hundred transducers in order to sufficiently surround the breast. Table 1, below lists a few non-limiting examples of the number of transducers and the number of rows of transducers that have been found to be suitable for use with the device of the present invention in various standard bra cup sizes, assuming 7.5 mm diameter transducers are employed.

TABLE 1

| Bra Cup Size | Rows of Transducers | Number of Transducers |
|---|---|---|
| A | 7 | 43 |
| B | 8 | 50 |
| C | 9 | 57 |
| D | 11 | 71 |

The ultrasound transducer array preferably comprises ultrasonic transducers sufficiently small so as to maximize the spatial resolution of the array, but not so small as to increase ultrasound beam diameter within the breast tissue because such an increase can lead to poor resolution. The device preferably detects tissue abnormalities in the breast as small as 5 mm in diameter. Thus, it has been found that transducers having a diameter of between about 5 mm and about 10 mm are generally suitable for such detection, although other size transducers may certainly be used. In some cases, it may be desirable to provide the transducer with focusing lenses to help form the signal from the transducer. The transducers 28 may also operate at any suitable frequency, although a frequency between about 1 MHz and about 10 MHz has been found to be highly effective for examining human breast tissue in terms of low attenuation and high spatial resolution.

The transducers 28 may be triggered all together, in groups or individually. In preferred embodiments, the transducers 28 are triggered individually and sequentially to reduce a multiple beam overlapping and thus, so more readily pinpoint the exact location of any abnormality in the tissue. In order to improve the resolution of the system, it may also be desirable to configure the device 1 such that transmitting transducers and receiving transducers are alternately arrayed on opposing sides of the breast. This allows for signals to be sent through the tissue in both directions. Alternatively, transducers 28 may be employed that are capable of both sending and receiving signals.

As noted above, the transducers 28 are preferably activated once the bladder pressure reaches a predetermined level. Preferably, the transducer driver 31 triggers each transducer 28 in the transmission array individually and in sequence to produce an ultrasonic pulse directed through the breast tissue and toward the paired receiving transducer. In preferred embodiments, some time delay is provided between each ultrasonic pulse to allow the ultrasonic noise to subside below a threshold level. This method is called time gating. Time gating can help reduce undesirable noise in the signals and help ensure that signals indicative of tissue abnormalities are discernable. It has been found that a suitable time between pulses can be between about 1 ms and about 100 ms. The pulse duration is preferably in the range of about 100 nanoseconds to about 500 nanoseconds.

Exemplary suitable ultrasound transducers are available as videoscan immersion type transducers, V303-SU-F1 type from Panametrics Inc. of Waltham, Mass.; piezocomposite transducers from MSI of Littleton, Mass.; and APC 850 type transducers from American Piezo Ceramics (Mackeyville, Pa.). Alternatively, MEMS (Micro Electro Mechanical System) based ultrasound transducers can be used to improve spatial resolution within a limited space. As an example, a suitable MEMS based capacitive ultrasound transducer is available as L-STD-1 from the Sensant Corporation of San Leandro, Calif. (U.S. Pat. Nos., 5,619,476, 5,870,351, 5,894,452, 5,982,709). Since the MEMS transducers are very small, a greater number of them may be used in a relatively closer spacing, resulting in an improvement in resolution, allowing the detection of smaller tissue abnormalities. Thus, such transducers are advantageous for several reasons, including their small size, low profile, high sensitivity, and wide frequency range.

Figure 10:
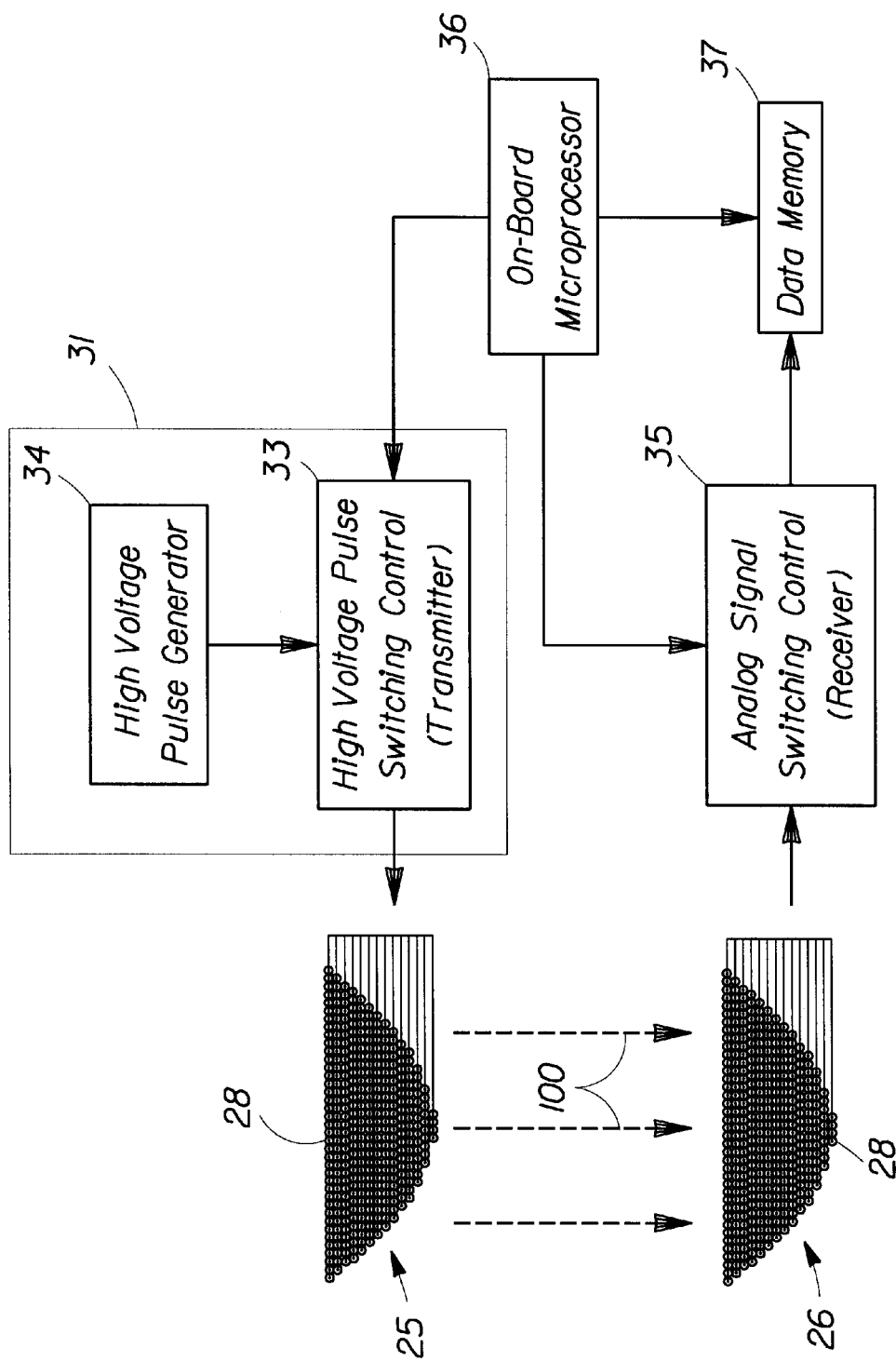
FIG. 10 is a block diagram of one embodiment of a system that can be used to trigger a transmitting transducer array and receive signals from a receiver transducer array.

The transducers 28 of the present invention are preferably driven by a transducer driver 31, a simple exemplary block diagram of which is shown in FIG. 10. The transducer driver 31 may be a separate element that is operatively connected to the wearable portion or may be an integral part of the wearable portion of the device 1. If the transducer driver 31 is a separate element, the transducer driver 31 may be housed in a container such as housing 32 shown in FIG. 1. This configuration allows the wearable portion of the device 1 to be lighter in weight and more conformable to the shape of the wearer.

As shown in FIG. 10, the transducer driver 31 may include an on-board microprocessor 36, switching control circuitry adapted to deliver a high voltage pulse 33, and high voltage pulse source 34 to trigger ultrasound transducers 28. In embodiments wherein the transmitting transducer array 25 is operating in pulse mode, the ultrasound transducers 28 may be activated by a high voltage spike. The high voltage spike is generated from the high voltage source 34 that may include a high voltage dc source and a capacitor. At the direction of the microprocessor 36 and switching control circuitry 33, high voltage stored in the capacitor is discharged and delivered to the transducers to trigger an ultrasound pulse. This triggering pulse typically has a falling edge of a voltage spike. It has been found that a suitable amplitude of such a spike can be in the range of about 360 and about 400 volts, but other amplitudes are contemplated and may be preferred for other uses or with different equipment. In such embodiments, the pulse duration is preferably in the range of about 100 nanoseconds to about 500 nanoseconds. Although not limited to the following, it has been found that the total electrical power delivered to each transducer may be between about 12 Watts and about 16 Watts if the transducer has 10 k ohm resonance impedance. Accordingly, it has been found that the total energy delivered may be between about 1.3 micro Joules and about 8 micro Joules.

In the embodiment shown in FIG. 10, the microprocessor 36 sets the address of the individual transducer 28 that should be triggered within the array 25 and sends it to the switching control 33. The switching control circuitry has a direct hardware connection to both high voltage source 34 and transducer array 25. Switching control circuitry 33 preferably includes a programmable gate array such as an FPGA (Field Programmable Gate Array) for address decoding and command interfacing between the microprocessor 36 and the switching circuitry 33. It is also preferable that the switching circuitry 33 includes a high voltage switching transistor or similarly functioning semiconductor switching array so that upon the receipt of discharge enable signal from microprocessor, it discharges high voltage stored at high voltage pulse generator 34.

Once triggered, the transducer 28 generates ultrasonic waves 100 by vibration (e.g. axial vibration of a piezioceramic transducer). After passing through the breast tissue and coupling structure, the waves 100 arrive at the receiving transducer array 26. The receiving transducers convert the ultrasonic waves 100 into an electrical signal which is eventually stored in memory. In some embodiments, all of the transducers 28 within the receiving array 26 can be operated at the same time, and thus, more than one receiving transducer may detect the ultrasonic waves from the transmitting transducer. However, in such embodiments, the signal switch 35 can select the specific receiving transducer matched with its corresponding transmitting transducer with information relating to the addresses of the transducers from microprocessor 36. In other embodiments, only the receiving transducer that is matched with the transmitting transducer is operated at the time the transmitting transducer is signaled. In either case, there is preferably a one-to-one correspondence of each transducer pair of transmitting and receiving arrays 25, 26.

The microprocessor 36 may be used to save and/or process the signals generated and/or received by the transducer 28 in any way desired by the user. For example, the operating program run by the microprocessor 36 can be written to detect a drop (depending on the tissue density) in the ultrasound transmission power compared to neighboring tissue. (Any sudden or abrupt changes in the peak amplitude profile may indicate a potentially abnormal tissue structure, which could be indicative of a hard mass or tumor.) In one embodiment, a drop of at least about 30% has been found to be suitable for detection of hard masses and/or tumors in human breast tissue.

Figure 11:
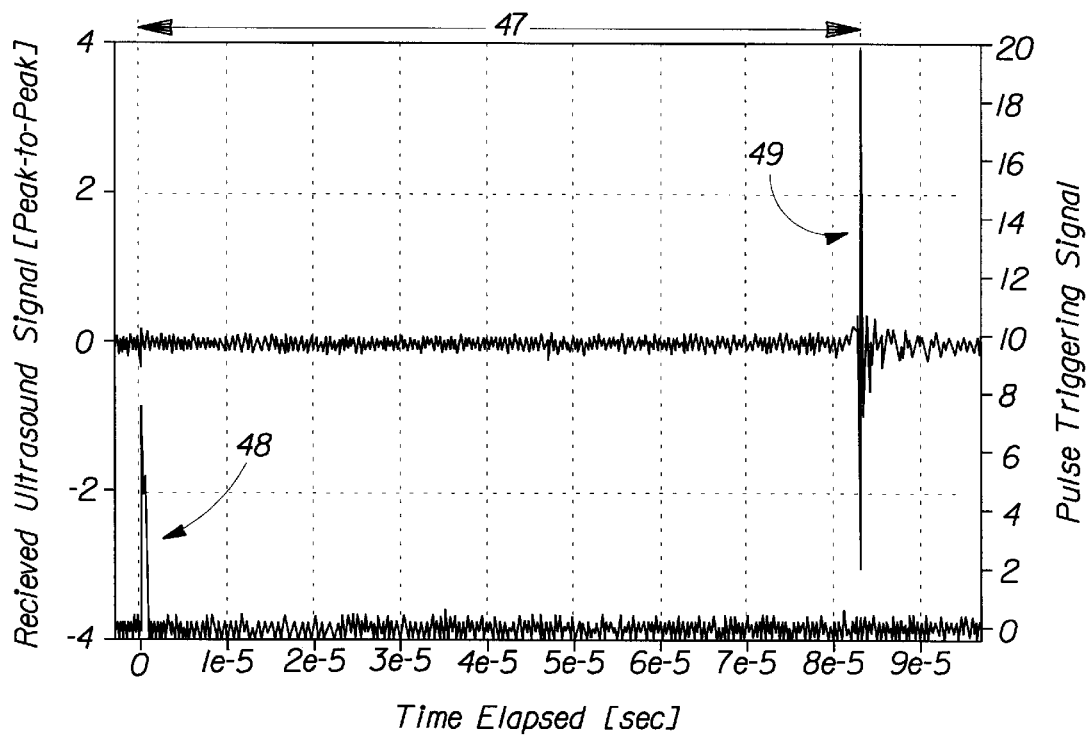
FIG. 11 is a graphical representation of the time-domain profile of an ultrasonic signal.

The microprocessor 36 may also be programmed to check the time-of-flight (TOF) for each detected signal. The TOF represented by the number 47 is defined as a time interval from the time the transmitting transducer is triggered to the moment the signal is received at the corresponding receiving transducer. As an example, FIG. 11 shows the time-domain profile of the transmitted ultrasound signal. In the plot of FIG. 11, the total transmission TOF is the time indicated by the number 47. The transducer triggering signal is indicated by the number 48 and the arrival of the transmitted signal is indicated by the number 49. Monitoring the TOF can also help determine the nature of the abnormality (e.g., cyst or hard mass). For example, a shorter TOF or higher transmission speed of ultrasound waves, compared to the surrounding tissue under examination generally indicates a harder or denser inclusion in the breast tissue. In embodiments where the transmitting and receiving ultrasonic transducer pairs may have different separation distances, the microprocessor 36 may also run a program to compensate for the different degree of signal attenuation due to non-uniform path lengths of the ultrasound signals.

The microprocessor 36 can be any suitable microprocessor such as Texas Instruments TMS320C1X series, the Motorola DSP5600 series, the Analog Devices ADSP-218X series, the Lucent Technologies ADSP32C series. The microprocessor 36 may be part of the transducer driver 31 or a separate device. Further, the microprocessor 36 and its supporting electronics may be integral with the wearable portion of the examination device 1 or may be a separate element operatively connected to the device 1. For example, the microprocessor 36 may be located in the housing 32 and joined to the support element 2 by wires. Alternatively, the microprocessor 32 can be remotely located from the examination device 1 (e.g. different room or building) and connected to the examination device 1 by wires, by radio (RF) waves or light waves (IR), depending on the environment in which the device 1 is used.

The examination device 1 may also include a data port adapted to transmit the data or diagnosis to a physician, computer, or website. Suitable data ports include telephone jacks, USB ports, serial ports, parallel ports, infrared or radio frequency transmitters, and the like.

The power supply for the examination device 1 or any portion of the device 1 may be any power supply known in the art suitable for such use. The power source may be a standard AC wall power or a battery. However, for wearable embodiments of the present invention, it is generally preferred that the device be powered via a battery which may be disposable or rechargeable.

Figure 12:
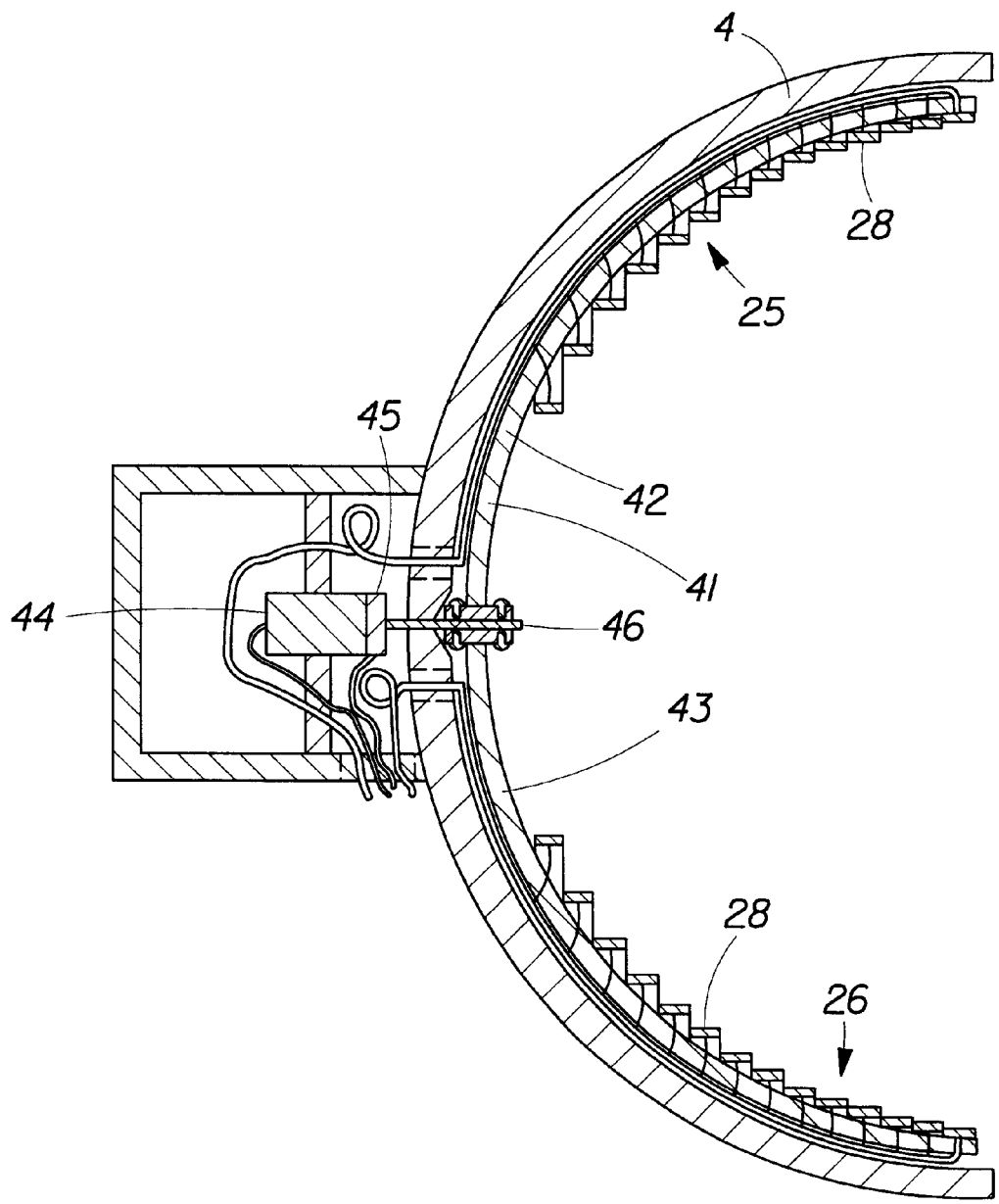
FIG. 12 is an enlarged, cross-sectional view of an alternative embodiment of the present invention including a rotating armature.

In an alternative embodiment of the present invention, as shown in FIG. 12, the transducers 28 are mounted on a curved armature 41, which is disposed within the shell 4. The armature 41 preferably includes two oppositely installed arms 42 and 43 having transducers 28 disposed thereon such that the faces of the transducers on the first arm 42 of the armature 41 are oriented towards the faces of the transducers 28 on the second arm 43 of the armature 41. The armature 41 is adapted to rotate in discrete steps about the wearer's breast in order to scan the breast from different angles. In a preferred embodiment, the armature 41 is capable or rotating completely about the breast to scan the breast from all angles, however, a lesser amount of rotation is possible to still give acceptable results.

As shown in FIG. 12, a motor 44 or other means for rotating the armature 41 is provided. The motor 44 may be located in the shell 4 or in a structure joined to the shell 4. Alternatively, the motor 44 can be located remotely from the shell and joined therewith via a flexible shaft, belt gear or other means for connecting the motor 44 to the armature 41. For example, a flexible drive shaft, such as a Ready-Flex shaft available from S.S. White, Piscataway, N.J. can be connected to the motor 44 to drive the armature 41.

Preferably, the motor 44 is relatively small compared to the examination device 1, but provides enough high torque to drive the armature 41 with transducers 28. One example of a suitable motor is the 512 CPR motor form MicroMo Electronics of Clearwater, Fla.

It is also preferred that the motor 44 has a position encoder 45 on the motor shaft 46, so the microprocessor 36 can determine the angular position of the armature 41 during scanning. The microprocessor 36 preferably reads the position encoder signal representing the angular increment. The angular position and transducer position along the curved armature 41 can be used to determine the spatial coordinate of any particular transducer position. This information, in turn, can be used to determine in which memory location the current ultrasound transmission data will be saved, facilitating the calculation of the exact location of the abnormality within the breast.

In general, an embodiment including a curved, rotating armature requires fewer transducers 28 in the first and second transducer arrays 25 and 26 than the stationary embodiments shown in FIG. 4 because the transducers 28 on the armature 41 are rotated about the breast rather than having to surround the breast. Thus, for example, a single column of transducers may be rotated about the breast to examine from almost any angle. However, the number of rows of transducers 28 located on the armature 41 may be the same or similar to preferred number of rows described with respect to the stationary array embodiment, above. Further, the rotating curvature embodiment can provide a tomographic rendering of the ultrasound transmission profile similar to the stationary radially symmetrical transducer array embodiment shown in FIG. 9B. However, the output may be derived from a smaller number of transducers 28. This can reduce the cost of the device as well as the weight of the wearable portion.

Preferably, as shown in FIG. 12, the armature 41 is rotated in one direction in a series of discrete steps through at least 180 degrees of arc to cover entire volume of breast tissue. The steps may be measured in terms of angle of rotation or actual arc path length at the transducer position. The steps may vary in size based on the size of the breast and the minimum size of the inclusion to be detected (i.e., the resolution). For example, in order to detect a 5 mm diameter inclusion wherein the distance between the transmitting and receiving transducer arrays is about 130 mm, each scanning angular increment is approximately 4.5 degrees of rotation. After the armature 41 moved a discrete angular increment (i.e., step), each transmitting transducer 28 in the transducer array on the armature 41 is preferably triggered in series until all of the transmitting transducers have been triggered. Once this is done, the armature 41 preferably moves to the next predetermined location and the transducers 28 are triggered again. The size and frequency of the transmitters can be similar to those described in the stationary embodiment. Further, the same time gating 40 can be utilized to improve the efficacy of the results obtained from the examination.

In embodiments of the present invention wherein the transducers are configured to provide radially symmetrical transmission paths, (e.g. the curved armature embodiment and the stationary embodiment of FIG. 9B), the tomographic transmission profile of breast tissue may be obtained. One example of a cross-sectional image made from the data obtained from an embodiment of the present invention employing radially symmetrical transmission paths is shown in FIG. 13. The shading pattern in the result shows relative variation in the ultrasound transmission profile. The dark shaded area 50 in the middle indicates local drop in the transmission that would be indicative of a tissue abnormality. The cross-sectional transmission profiles generated from the transducer pairs of embodiments employing radially symmetrical transmission paths can be combined to render a three-dimensional tomographic transmission profile of the tissue.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A breast tissue examination device, at least a portion of which is adapted to be worn by a wearer, the device comprising:

a support element adapted to fit over at least a portion of a breast of the wearer, the support element including:
a shell having an opening, a perimeter defined by the opening, an inner surface that faces the breast of the wearer during use and an outer surface opposed to the inner surface;
a measurement apparatus including at least two mutually opposed ultrasound transducer arrays, the transducer arrays being disposed on at least a portion of the inner surface of the shell; and
at least one bladder element disposed adjacent at least a portion of one of the mutually opposed ultrasound transducer arrays and/or the inner surface of the shell, the bladder configured so as to orient the wearer's breast for examination;

means for operatively connecting the two mutually opposed transducer arrays to a transducer driver; and means for holding the support element on the wearer during use.

2. The device of claim 1 wherein each of the mutually opposed ultrasound transducer arrays comprises a multiplicity of ultrasound transducers.

3. The device of claim 2 wherein the ultrasound transducers are arranged as opposing pairs of transducers, each opposing pair comprising a first transducer having a first transducer face and a second transducer having a second transducer face, wherein the first transducer face is parallel the second transducer face.

4. The device of claim 1 wherein the transducer arrays are disposed on a series of concentric ridges disposed on the inner surface of the shell.

5. The device of claim 1 wherein the transducer arrays each comprise both ultrasonic transmitting transducers and ultrasonic receiving transducers.

6. The device of claim 1 wherein one of the transducer arrays comprises ultrasonic transmitting transducers and the other of the transducer arrays comprises ultrasonic receiving transducers.

7. The device of claim 1 wherein the transducer arrays are arranged in a parallel array pattern or a radially symmetric array pattern.

8. The device of claim 1 wherein the bladder is filled with an acoustic transmission medium.

9. The device of claim 1 wherein the acoustic transmission medium includes water, silicone and/or oil.

10. The device of claim 1 wherein the bladder is fillable with an acoustic transmission medium and the device further includes a reservoir for holding the acoustic transmission medium when the acoustic transmission medium is not in the bladder.

11. The device of claim 1 further comprising a cushion deposed along at least a portion of the perimeter of the shell, the cushion adapted to form a seal against the wearer during use.

12. The device of claim 1 further including an insert disposed between the bladder and the wearer's breast during use.

13. The device of claim 1 further including a microprocessor for processing data generated by the transducers.

14. The device of claim 1 wherein the two mutually opposed transducer arrays are mounted on opposing ends of a curved armature.

15. The device of claim 14 wherein the curved armature is rotatable within the shell.

16. The device of claim 1 wherein the means for holding the support element on the wearer during use includes a strap.

17. The device of claim 16 wherein the supporting element includes two shells, and wherein the two shells are joined together such that the support element forms a brassiere-like structure including the straps and shells that can be worn by the wearer as a brassiere is worn.

18. The device of claim 1 wherein the support element includes at least two bladders.

19. The device of claim 1 wherein at least a portion of the device is operatively joined to a non-wearable element and wherein the non-wearable element includes one or more of the following: a reservoir for holding the acoustically conductive liquid, a microprocessor and/or a power supply.

20. A device to examine the breast of a wearer, the device comprising:
   a) a shell having an opening, a perimeter defined by the opening, an inner surface that faces the breast of the wearer during use, an outer surface opposed to the inner surface, and a bisecting plane dividing the shell into a first half and a second half;
   b) a first ultrasonic transducer array disposed adjacent the inner surface of the shell first half, the array comprising:
      i) a plurality of ultrasonic transmitting transducers each having a transmitting surface, the transmitting surface of the transducers being aligned perpendicular to the bisecting plane;
      ii) a means for electronically controlling the first transducer array;
   c) a second ultrasonic transducer array disposed adjacent the inner surface of the shell second half, the array comprising:
      i) a plurality of ultrasonic receiving transducers each having a receiving surface, the receiving surface of the transducers being aligned perpendicular to the bisecting plane, each of the receiving transducer being capable of receiving an ultrasonic signal from at least one oppositely aligned transmitting transducer;
      ii) a means for electronically controlling the second transducer array;
   d) a first flexible bladder disposed in at least a portion of the first half of the shell, the first flexible bladder capable of being independently and controllably filled with an acoustic transmission medium, thereby forming a substantially airless seal between the first transducer array and the wearer's breast;
   e) a second flexible bladder disposed in at least a portion of the second half of the shell, the second flexible bladder capable of being independently and controllably filled with an acoustic transmission medium, thereby orienting the wearer's breast and further forming a substantially airless seal between the second transducer array and the wearer's breast; and
   f) an apparatus for originating an acoustical signal at the transmitting transducers and processing the signal received by the receiving transducers.

21. The device of claim 20 wherein the first and second ultrasonic transducer arrays are disposed on a series of concentric ridges disposed on the inner surface of the shell.

22. The device of claim 20 wherein the transducer arrays are arranged in a parallel array pattern or a radially symmetric array pattern.

23. The device of claim 20 wherein the acoustic transmission medium includes water, silicone and/or oil.

24. The device of claim 20 further comprising a cushion deposed along at least a portion of the perimeter of the shell, the cushion adapted to form a seal against the wearer during use.

25. The device of claim 20 further including an insert disposed between the bladder and the wearer's breast during use.

26. The device of claim 20 further including a microprocessor for processing signal received by the receiving transducers.

27. The device of claim 20 wherein the two mutually opposed transducer arrays are mounted on opposing ends of a curved armature.

28. The device of claim 27 wherein the curved armature is rotatable within the shell.

29. The device of claim 20 wherein the supporting element includes two shells, and wherein the two shells are joined together such that the support element forms a brassiere-like structure which is held on the wearer by straps.

30. The device of claim 20 wherein at least a portion of the device is operatively joined to a non-wearable element and wherein the non-wearable element includes one or more of the following: a reservoir for holding the acoustically conductive liquid, a microprocessor and/or a power supply.

* * * * *